US012802821B2

(12) United States Patent
Williams et al.

(10) Patent No.: US 12,802,821 B2
(45) Date of Patent: Nov. 17, 2026

(54) VALIDATION OF HEALTH STATUS INFORMATION

(71) Applicant: Quantum Materials Corp., San Marcos, TX (US)

(72) Inventors: Jay M. Williams, Austin, TX (US); Stephen Squires, San Marcos, TX (US)

( * ) Notice: Subject to any disclaimer, the term of this patent is extended or adjusted under 35 U.S.C. 154(b) by 377 days.

(21) Appl. No.: 17/221,736

(22) Filed: Apr. 2, 2021

(65) Prior Publication Data

US 2021/0313069 A1 Oct. 7, 2021

Related U.S. Application Data

(60) Provisional application No. 63/025,143, filed on May 14, 2020, provisional application No. 63/013,522, (Continued)

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0022* (2013.01); *G16H 10/40* (2018.01); *G16H 10/60* (2018.01); *G16H 15/00* (2018.01); *G16H 80/00* (2018.01)

(58) Field of Classification Search
CPC ........ G16H 50/30; G16H 10/40; G16H 10/60; G16H 15/00; G16H 80/00; A61B 5/0022
See application file for complete search history.

(56) References Cited

U.S. PATENT DOCUMENTS

| | | | |
|---|---|---|---|
| 5,613,140 | A | 3/1997 | Taira |
| 5,652,192 | A | 7/1997 | Matson et al. |

(Continued)

FOREIGN PATENT DOCUMENTS

| | | | |
|---|---|---|---|
| AU | 2020101208 | A4 | 8/2020 |
| CN | 102031110 | A | 4/2011 |

(Continued)

OTHER PUBLICATIONS

Heindel, Tobias, et al. "Quantum Key Distribution Using Quantum Dot Single-Photon Emitting Diodes in the Red and near Infrared Spectral Range." New Journal of Physics, IOP Publishing and Deutsche Physikalische Gesellschaft, Aug. 2, 2012, iopscience.iop.org/article/10.1088/1367-2630/14/8/083001. (Year: 2012).*

(Continued)

*Primary Examiner* — Sheetal R Paulson

(57) ABSTRACT

A method, system, and apparatus, including a program encoded on computer-readable medium, for displaying health status information on a display of a mobile device and detecting encoded data on the mobile device using an image sensor. The encoded data includes a reference to a digital token previously stored in a distributed ledger to record at least one health-related event associated with the displayed health status information. A serialized representation of the detected encoded data is transmitted to a server system. The server system is adapted to retrieve corresponding health status information and authenticate the retrieved health status information based on the digital token. A communication is received from the server system providing verification of the health status information.

18 Claims, 6 Drawing Sheets

Related U.S. Application Data filed on Apr. 21, 2020, provisional application No. 63/004,486, filed on Apr. 2, 2020.

(51) Int. Cl.

| | |
|---|---|
| ***G16H 10/40*** | (2018.01) |
| ***G16H 10/60*** | (2018.01) |
| ***G16H 15/00*** | (2018.01) |
| ***G16H 80/00*** | (2018.01) |

(56) References Cited

U.S. PATENT DOCUMENTS

| | | | | |
|---|---|---|---|---|
| 6,179,312 | B1 | 1/2001 | Paschke et al. | |
| 6,179,912 | B1 | 1/2001 | Barbera-Guillem et al. | |
| 6,207,229 | B1 | 3/2001 | Bawendi et al. | |
| 6,225,198 | B1 | 5/2001 | Alivisatos et al. | |
| 6,576,291 | B2 | 6/2003 | Bawendi et al. | |
| 6,708,618 | B1 | 3/2004 | Tsai | |
| 6,815,064 | B2 | 11/2004 | Treadway et al. | |
| 6,872,249 | B2 | 3/2005 | Peng et al. | |
| 6,878,871 | B2 | 4/2005 | Scher et al. | |
| 7,267,810 | B2 | 9/2007 | Yu et al. | |
| 7,393,516 | B2 | 7/2008 | Seo et al. | |
| 7,833,506 | B2 | 11/2010 | Rauscher et al. | |
| 8,133,932 | B2 | 3/2012 | Kijlstra et al. | |
| 9,577,149 | B2 | 2/2017 | Lu et al. | |
| 9,922,224 | B1 | 3/2018 | Nambudiri | |
| 11,209,428 | B1 | 12/2021 | Robinson et al. | |
| 2002/0083888 | A1 | 7/2002 | Zehnder et al. | |
| 2004/0118448 | A1 | 6/2004 | Scher et al. | |
| 2004/0247517 | A1 | 12/2004 | Zehnder et al. | |
| 2005/0016851 | A1 | 1/2005 | Jensen et al. | |
| 2005/0112849 | A1 | 5/2005 | Stott et al. | |
| 2005/0135079 | A1 | 6/2005 | Yin Chua et al. | |
| 2005/0164227 | A1 | 7/2005 | Ogura et al. | |
| 2005/0238568 | A1 | 10/2005 | Yu et al. | |
| 2007/0132052 | A1 | 6/2007 | Sargent et al. | |
| 2008/0199851 | A1 | 8/2008 | Egan et al. | |
| 2008/0241051 | A1 | 10/2008 | Scher et al. | |
| 2008/0299046 | A1 | 12/2008 | White et al. | |
| 2008/0312847 | A1 | 12/2008 | Safai et al. | |
| 2009/0263496 | A1 | 10/2009 | Kijlstra et al. | |
| 2009/0295005 | A1 | 12/2009 | Rauscher et al. | |
| 2010/0027192 | A1 | 2/2010 | Perry et al. | |
| 2010/0068522 | A1 | 3/2010 | Pickett et al. | |
| 2010/0133418 | A1 | 6/2010 | Sargent et al. | |
| 2010/0217538 | A1 | 8/2010 | Safai et al. | |
| 2011/0163854 | A1 | 7/2011 | Hamelin et al. | |
| 2011/0275912 | A1 | 11/2011 | Boyden et al. | |
| 2014/0034121 | A1 | 2/2014 | Rauscher et al. | |
| 2014/0254796 | A1 | 9/2014 | Li et al. | |
| 2014/0326921 | A1 | 11/2014 | Lu et al. | |
| 2015/0039338 | A1 | 2/2015 | Tregnaghi | |
| 2016/0203276 | A1 | 7/2016 | Castellano | |
| 2017/0086676 | A1 | 3/2017 | Flitsch et al. | |
| 2017/0122866 | A1 | 5/2017 | Safai et al. | |
| 2017/0166808 | A1 | 6/2017 | Lu et al. | |
| 2017/0173262 | A1* | 6/2017 | Veltz | G16H 20/17 |
| 2017/0209102 | A1 | 7/2017 | Parthasarathy et al. | |
| 2017/0264836 | A1 | 9/2017 | Mandelli et al. | |
| 2018/0211718 | A1 | 7/2018 | Heath | |
| 2019/0003974 | A1 | 1/2019 | Moynihan et al. | |
| 2019/0126265 | A1 | 5/2019 | Weigl et al. | |
| 2019/0147137 | A1* | 5/2019 | Gergely | H04L 9/3226 705/51 |
| 2019/0164160 | A1 | 5/2019 | Zamora Duran et al. | |
| 2019/0191049 | A1 | 6/2019 | Yu | |
| 2020/0167622 | A1 | 5/2020 | Sinha et al. | |
| 2020/0198384 | A1 | 6/2020 | Bollstrom et al. | |
| 2020/0202751 | A1 | 6/2020 | Chen | |
| 2020/0294634 | A1* | 9/2020 | Katz | G16H 50/30 |
| 2020/0311646 | A1 | 10/2020 | Koenig et al. | |
| 2021/0073882 | A1 | 3/2021 | Park | |
| 2021/0080393 | A1 | 3/2021 | Williams et al. | |
| 2021/0280315 | A1* | 9/2021 | Woldenberg | G16H 10/20 |
| 2021/0287770 | A1* | 9/2021 | Anderson | H04L 67/02 |
| 2021/0302428 | A1* | 9/2021 | Stone | G16H 10/60 |
| 2021/0385921 | A1 | 12/2021 | Roy et al. | |
| 2022/0060676 | A1 | 2/2022 | Scheller | |
| 2022/0139510 | A1* | 5/2022 | Romanychev | G06F 21/36 705/2 |
| 2022/0349883 | A1 | 11/2022 | Robinson et al. | |
| 2022/0349884 | A1 | 11/2022 | Robinson et al. | |
| 2022/0404354 | A1 | 12/2022 | Robinson et al. | |

FOREIGN PATENT DOCUMENTS

| | | | |
|---|---|---|---|
| DE | 102006017696 | A1 | 10/2007 |
| DE | 102006055218 | A1 | 5/2008 |
| EP | 1452225 | A1 | 9/2004 |
| JP | H07204298 | A | 8/1995 |
| JP | 2003192344 | A | 7/2003 |
| JP | 2003193119 | A | 7/2003 |
| JP | 2003225900 | A | 8/2003 |
| JP | 2004202406 | A | 7/2004 |
| JP | 2005060132 | A | 3/2005 |
| JP | 2005125280 | A | 5/2005 |
| JP | 2007069162 | A | 3/2007 |
| JP | 2007204298 | A | 8/2007 |
| JP | 2007537886 | A | 12/2007 |
| WO | WO-9710175 | A1 | 3/1997 |
| WO | WO-9802237 | A1 | 1/1998 |
| WO | WO-0107689 | A2 | 2/2001 |
| WO | WO-02053810 | A1 | 7/2002 |
| WO | WO-03081683 | A1 | 10/2003 |
| WO | WO-2005020659 | A2 | 3/2005 |
| WO | WO-2005052996 | A2 | 6/2005 |
| WO | WO-2005106082 | A1 | 11/2005 |
| WO | WO-2008061632 | A1 | 5/2008 |
| WO | WO-2012035005 | A1 | 3/2012 |
| WO | WO-2013079423 | A1 | 6/2013 |
| WO | WO-2018207180 | A1 | 11/2018 |
| WO | WO-2021055645 | A1 | 3/2021 |
| WO | WO-2021203059 | A1 | 10/2021 |
| WO | WO-2022235629 | A1 | 11/2022 |
| WO | WO-2022236120 | A1 | 11/2022 |

OTHER PUBLICATIONS

P. M. Intallura, M. B. Ward, O. Z. Karimov, Z. L. Yuan, P. See, A. J. Shields, P. Atkinson, D. A. Ritchie; Quantum key distribution using a triggered quantum dot source emitting near 1.3μm Appl. Phys. Lett. Oct. 15, 2007; 91 (16): 161103. https://doi.org/10.1063/1.2799756 (Year: 2007).*

Aivaliotis, P. et al. (Aug. 2007) "Stark shift of the spectral response in quantum dots-in-a-well infrared photodetectors" J Phys D: Appl Phy, 40:5537-5540.

International Search Report and Written Opinion for International Application No. PCT/US2020/051333, dated Feb. 2, 2021, 10 pages.

International Search Report and Written Opinion for International Application No. PCT/US2021/025662, dated Jul. 16, 2021, 9 pages.

International Search Report and Written Opinion with Notification of Transmittal for International Application No. PCT/US2022/027414, dated Jun. 1, 2022, 7 pages.

International Search Report and Written Opinion with Notification of Transmittal for International Application No. PCT/US2022/028166, mailed Aug. 18, 2022, 9 pages.

Liu, B. et al. (Jul. 24, 2020) "Development of a quantum-dot lateral flow immunoassay strip based portable fluorescence smart-phone system for ultrasensitive detection of IgM/IgG to SARS-CoV-2", medRxiv, preprint, doi:https://doi.org/10.1101/2020.07.21.20159392; 18 pages.

Quantum Materials Corp. Quantum Materials Announces QDX™ HealthID to Support Back-to-Work "Immunization Passport" Programs. Apr. 13, 2020 [online]. Retrieved from the Internet: https://www.globenewswire.com/news-release/2020/04/13/2015143/0/en/Quantum-Materials-Announces-QDX-HealthID-to-Support-Back-to-Work-Immunization-Passport-Programs.html; 2 printed pages.

(56) References Cited

OTHER PUBLICATIONS

Rathnayake, N. et al. (Jan. 20, 2017) Salivary Diagnostics—Point-of-Care diagnostics of MMP-8 in dentistry and medicine. Diagnostics, 7(7):1-12; doi:10.3390/diagnostics7010007.
U.S. Appl. No. 17/024,640: Restriction Requirement, dated Sep. 21, 2022, 7 pages.
U.S. Appl. No. 17/321,194: Notice of Allowance, dated Oct. 4, 2021, 14 pages.
Wang, D. et al. (Dec. 2020) "Rapid lateral flow immunoassay for the fluorescence detection of SARS-CoV-2 RNA" Nature Biomedical Engineering, 4:1150-1158.
Wang, J. et al. (Apr. 2019) "Quantum Dot-Based Lateral Flow Test Strips for Highly Sensitive Detection of the Tetanus Antibody" ACS Omega, 4:6789-6795.
International Preliminary Report on Patentability for International Application No. PCT/US2021/025662, dated Sep. 29, 2022, 8 pages.
[Author Unknown] "A Guide to Recording Fluorescence Quantum Yields", Jobin Yvon Ltd. [online] http://www.horiba.com/fileadmin/uploads/Scientific/Documents/Fluorescence/quantumyieldstrad.pdf (Access Date: Oct. 5, 2011); 6 pages.
Barwick, V. J., "Strategies for solvent selection—a literature review", TrAC Trends in Analytical Chemistry (1997); 16(6): 293-309.
Battaglia, D., et al., "Formation of high quality InP and InAs nanocrystals in a noncoordinating solvent", Nano Letters (2002); 2(9): 1027-1030.
Burda, C., et al., "Chemistry and properties of nanocrystals of different shapes", Chemical Reviews (2005); 105(4): 1025-1102.
Byun, H., et al., "Facile consecutive solvothermal growth of highly fluorescent InP/ZnS core/shell quantum dots using a safer phosphorus source", Nanotechnology (2011); 22(23): 235605; 6 pages.
Dayal, S., et al., "Photovoltaic devices with a low band gap polymer and CdSe nanostructures exceeding 3% efficiency", Nano Letters (2010); 10(1): 239-242.
De Mello Donegá, C., et al., "Physicochemical evaluation of the hot-injection method, a synthesis route for monodisperse nanocrystals", Small (2005); 1(12): 1152-1162.
De Mello, J., et al., "Microscale reactors: nanoscale products", Lab Chip (2004); 4(2): 11N-15N.
Extended European Search Report for European Application No. EP11191589.8 dated May 31, 2012, 7 pages.
Final Office Action for U.S. Appl. No. 17/024,640 dated Aug. 11, 2023, 13 pages.
Haremza, J. M., et al., "Attachment of single CdSe nanocrystals to individual single-walled carbon nanotubes", Nano Letters (2002); 2(11): 1253-1258.
He, L. B., et al., "Size controlled synthesis of semiconductor nanocrystals in a continuous-flow mode microcapillary reactor", The European Physical Journal D (2009); 52: 15-18.
International Preliminary Report on Patentability for International Application No. PCT/EP2007/009677, dated Jun. 10, 2009, 14 pages.
International Preliminary Report on Patentability for International Application No. PCT/EP2011/065839, dated Mar. 19, 2013, 7 pages.
International Preliminary Report on Patentability for International Application No. PCT/EP2012/073552, dated Jun. 3, 2014, 6 pages.
International Preliminary Report on Patentability for International Application No. PCT/US2020/051333, dated Mar. 15, 2022, 8 pages.
International Search Report and Written Opinion for International Application No. PCT/EP2007/009677, dated Feb. 22, 2008, 15 pages.
International Search Report and Written Opinion for International Application No. PCT/EP2011/065839, dated Oct. 21, 2011, 9 pages.
International Search Report and Written Opinion for International Application No. PCT/EP2012/073552, dated Dec. 21, 2012, 8 pages.
Invitation to Pay Fee for International Application No. PCT/US2023/26707 dated Aug. 17, 2023, 3 pages.
Kawa, M., et al., "Large-scale production of CdSe nanocrystal by a continuous flow reactor", Journal of Nanoparticle Research (2003); 5: 81-85.
Landi, B. J., et al., "Noncovalent attachment of CdSe quantum dots to single wall carbon nanotubes", Materials Letters (2006); 60(29-30): 3502-3506.
Law, M., et al., "Structural, optical, and electrical properties of PbSe nanocrystal solids treated thermally or with simple amines", Journal of the American Chemical Society (2008); 130(18): 5974-5985.
Li, L., et al., "One-pot synthesis of highly luminescent InP/ZnS nanocrystals without precursor injection", Journal of the American Chemical Society (2008); 130(35): 11588-11589.
Murray, C. B., et al., "Synthesis and characterization of nearly monodisperse CdE (E= sulfur, selenium, tellurium) semiconductor nanocrystallites", Journal of the American Chemical Society (1993); 115(19): 8706-8715.
Nakamura, H., et al., "Application of a microfluidic reaction system for CdSe nanocrystal preparation: their growth kinetics and photoluminescence analysis", Lab on a Chip (2004); 4(3): 237-240.
Non-Final Office Action for U.S. Appl. No. 17/532,403 dated Sep. 12, 2023, 7 pages.
Notice of Acceptance for Australian Application No. AU2012344013 mailed Feb. 21, 2017, 3 pages.
Office Action for Australian Application No. AU2012344013 mailed Jul. 5, 2016, 3 pages.
Office Action for European Application No. EP07819686.2 mailed Jan. 31, 2018, 4 pages.
Office Action for European Application No. EP11755075.6 mailed Jan. 4, 2016, 5 pages.
Office Action for European Application No. EP12790906.7 mailed Mar. 5, 2018, 5 pages.
Office Action for Indian Application No. 3174/DELNP/2009 mailed Jun. 27, 2014, 3 pages.
Office Action for Israel Application No. IL198733 mailed Mar. 29, 2012, 3 pages.
Office Action for Japanese Application No. 2009-537505 mailed Jul. 17, 2012, 7 pages.
Office Action for Japanese Application No. 2009-537505 mailed Jul. 26, 2011, 5 pages.
Owen, J. S., et al., "Reaction chemistry and ligand exchange at cadmium- selenide nanocrystal surfaces", Journal of the American Chemical Society (2008); 130(37): 12279-12281.
Panthani, M. G., et al., "Synthesis of CulnS2, CulnSe2, and Cu (In×Ga1-x) Se2 (CIGS) nanocrystal "inks" for printable photovoltaics", Journal of the American Chemical Society (2008); 130(49): 16770-16777.
Reconsideration Report by Examiner before Appeal for Japanese Application No. 2009-537505 mailed Jan. 11, 2013, 6 pages.
Sun, B., et al., "Improved efficiency of photovoltaics based on CdSe nanorods and poly (3-hexylthiophene) nanofibers", Physical Chemistry Chemical Physics (2006); 8(30): 3557-3560.
Sun, B., et al., "Vertically segregated hybrid blends for photovoltaic devices with improved efficiency", Journal of Applied Physics (2005); 97(014914); 7 pages.
Trintade, T., et al., "Nanocrystalline semiconductors: Síntesis, properties, and perspectivas", Chemistry of Materials (2001); 13(11): 3843-3858.
U.S. Appl. No. 14/361,862: Declaration of Nathan E. Stott, signed Oct. 3, 2016; 5 pages.
U.S. Appl. No. 12/515,706: Notice of Allowance dated Jul. 14, 2010, 9 pages.
U.S. Appl. No. 14/050,189: Office Action dated Aug. 24, 2016, 12 pages.
U.S. Appl. No. 14/050,189: Office Action dated Jul. 28, 2017, 10 pages.
U.S. Appl. No. 14/050,189: Office Action dated Nov. 10, 2016, 4 pages.
U.S. Appl. No. 14/050,189: Office Action dated Sep. 16, 2015, 9 pages.
U.S. Appl. No. 14/361,862: Notice of Allowance, dated Oct. 14, 2016, 7 pages.
U.S. Appl. No. 14/361,862: Office Action, dated May 4, 2016, 8 pages.

(56) References Cited

OTHER PUBLICATIONS

U.S. Appl. No. 14/361,862: Office Action, dated Nov. 16, 2015, 8 pages.
U.S. Appl. No. 14/361,862: Restriction Requirement, dated Jun. 25, 2015, 7 pages.
U.S. Appl. No. 15/436,454: Office Action, dated Mar. 13, 2017, 7 pages.
U.S. Appl. No. 17/024,640: Office Action, dated Feb. 3, 2023, 8 pages.
U.S. Appl. No. 17/532,403: Office Action, dated Feb. 2, 2023, 6 pages.
U.S. Appl. No. 17/738,289: Restriction Requirement, dated Aug. 24, 2023, 6 pages.
Valera, F. E., et al., "The Flow's the Thing . . . Or Is It? Assessing the Merits of Homogeneous Reactions in Flask and Flow", Angewandte Chemie International Edition (2010); 49(14): 2478-2485.
Wan, Z., et al., "Size controlled synthesis of blue emitting core/shell nanocrystals via microreaction", The Journal of Physical Chemistry C (2011); 115(5): 1569-1575.
Xie, R., et al., "Colloidal InP nanocrystals as efficient emitters covering blue to near-infrared", Journal of the American Chemical Society (2007); 129(50): 15432-15433.
Xu, S., et al., "Rapid synthesis of highly luminescent InP and InP/ZnS nanocrystals", Journal of Materials Chemistry (2008); 18(23): 2653-2656.
Xu, S., et al., "Rapid synthesis of high-quality InP nanocrystals", Journal of the American Chemical Society (2006); 128(4): 1054-1055.
Yen, B. K. H., et al., "A microfabricated gas-liquid segmented flow reactor for high-temperature synthesis: the case of CdSe quantum dots", Angewandte Chemie International Edition (2005); 117(44): 5447-5451.
Zenkevich, E., et al., "Photophysical properties of self-aggregated porphyrin: semiconductor nanoassemblies", International Journal of Photoenergy (2006); 2006 (Article ID 90242): 1-7.
Ziegler, J., et al., "Silica-coated InP/ZnS nanocrystals as converter material in white LEDs", Advanced Materials (2008); 20(21): 4068-4073.

* cited by examiner

VALIDATION OF HEALTH STATUS INFORMATION

RELATED APPLICATIONS

This application claims the benefit of U.S. Provisional Application No. 63/004,486 filed Apr. 2, 2020, U.S. Provisional Application No. 63/013,522 filed Apr. 21, 2020 and U.S. Provisional Application filed May 14, 2020, all of which are incorporated herein by reference in their entirety.

BACKGROUND

This description relates to verifying health-related information, and more particularly to validation of health status information.

Visibility into the test status of individuals for specific diseases, such as the COVID-19 coronavirus, is vital for coordinating healthcare responses and delivering treatment programs. Likewise, visibility into a person's health and immunization status is paramount when considering whether that individual should be allowed to socialize with others in the community and—crucially—the workforce.

While such visibility is a fundamental requirement to address both population health and economic rebuilding imperatives, it is only useful when it is based on processes and data that are trusted and provably accurate.

SUMMARY

In accordance with aspects described in this specification, health status information for a person or a location collected through testing, administration of immunizations, other healthcare-related processes, or safety procedures can be selectively shared with third parties in a manner that protects privacy of health information while enabling third parties to verify that the health status information is authentic and complies with certain certifications or desired sets of criteria. Events that occur in an overall process of obtaining health status information can be tracked and memorialized using a digital token stored in a distributed ledger so that the occurrence of the event can later be authenticated and verified. Identification information for the people, entities, equipment, immunization doses, medications, test kits, or other objects can also be tracked and recorded using the same digital token or another digital token stored in the distributed ledger. Subsequently, the occurrence of the events and the people, entities, and objects associated with events can be authenticated and verified by accessing the digital tokens stored in the distributed ledger.

A software application installed on a first user's mobile device (e.g., a smartphone or a tablet) can display health status information (e.g., indicating that the first user has received a particular vaccination or completed a specific diagnostic testing regimen) on a display of the mobile device. The displayed information may include optically detectable encoded information (e.g., a QR-code) that can be captured as an image by the camera or other image sensor on a second user's mobile device (e.g., belonging to a person who wants to verify the health status information). A software application on the second user's mobile device can decode the captured image to identify a digital token associated with the encoded information. The software application can cause the second user's mobile device to transmit the digital token to a server system associated with the software application. The server system can authenticate the digital token against data stored in the distributed ledger and return information to the second user's mobile device verifying the authenticity of the health status information. The returned information can include the health status information (e.g., so that the second user can confirm that it matches the health status information displayed on the first user's mobile device), an image of the person associated with the health status information (e.g., so that the second user can confirm that it matches the first user), and other identification or verification information (e.g., a name and/or a timestamp for when the health status information was last updated).

In accordance with aspects of this specification, health status information is displayed on a display of a mobile device. Encoded data is detected on the mobile device using an image sensor. The encoded data includes a reference to a digital token previously stored in a distributed ledger to record at least one health-related event associated with the displayed health status information. A serialized representation of the detected encoded data is transmitted to a server system. The server system is adapted to retrieve corresponding health status information and authenticate the retrieved health status information based on the digital token. A communication is received from the server system providing verification of the health status information.

Implementations can include one or more of the following features. The communication includes a verification of an identity of at least one individual associated with the health status information. The verification includes a verification that the health status information complies with a predetermined set of criteria for determining the health status information. The predetermined set of criteria defines a verified chain of possession of at least one of a health test kit or a vaccination dose. The predetermined set of criteria defines a predetermined period of time since a positive test result for a communicable disease. The predetermined set of criteria defines a verified source of at least one of a health test kit or a vaccine. The predetermined set of criteria defines a recordation of a sequence of events in a distributed ledger. The health status information identifies at least one of the following: receipt of a vaccination; a positive antibody test; passage of a predetermined period of time since a positive test result for a communicable disease; a certification from an authorizing authority; or a quarantine status. The communication includes a verification that at least one of a vaccination or a health test was administered by an authorized entity. The health status information corresponds to a selected health status profile of a plurality of health status profiles for an individual. Each health status profile associated with a different set of criteria for determining the health status information for the corresponding health status profile of the plurality of health status profiles. The selected health status profile corresponding to the health status information is selected by a user of the mobile device.

In accordance with additional aspects of this specification, a system includes a database storing records associated with a plurality of registered users and a server system communicably connected to the database. The server system is adapted to receive a request from a first remote device for a verification of health status information displayed on a second remote mobile device. The request is sent by the first remote device in response to detecting encoded data displayed on the second remote mobile device. The encoded data includes a reference to a digital token previously stored in a distributed ledger to record at least one health-related event associated with the health status information, and the request includes the reference to the digital token. The server system is further adapted to retrieve health status information corresponding to the digital token, authenticate the retrieved health status information using the distributed ledger based on the digital token, and transmit a communication to the first remote device providing verification of the health status information.

Implementations can include one or more of the following features. The system includes the first remote device and the second remote mobile device. The first remote device comprises a mobile device including the image sensor and includes a software application adapted to receive an image of a display of the second remote mobile device and to decode the encoded data. The second remote mobile device includes a software application adapted to allow a user of the second remote mobile device to selectively display the health status information.

In accordance with additional aspects of this specification, a computer storage medium is encoded with a computer program, and the program includes instructions that when executed by data processing apparatus cause the data processing apparatus to perform operations including detecting an image displayed on a display of a mobile device using an image sensor. The image is associated with health status information displayed on the display of the mobile device. The operations further include decoding data encoded in the detected image to obtain a reference to a digital token previously stored in a distributed ledger to record at least one health-related event associated with the health status information and sending a request to a server system for verification of the health status information. The request includes a serialized representation of the detected encoded data to a server system and the server system is adapted to authenticate the health status information based on the digital token. The operations also include receiving a communication from the server system providing verification of the health status information.

DESCRIPTION OF DRAWINGS

Like reference symbols in the various drawings indicate like elements.

DETAILED DESCRIPTION

Figure 1:
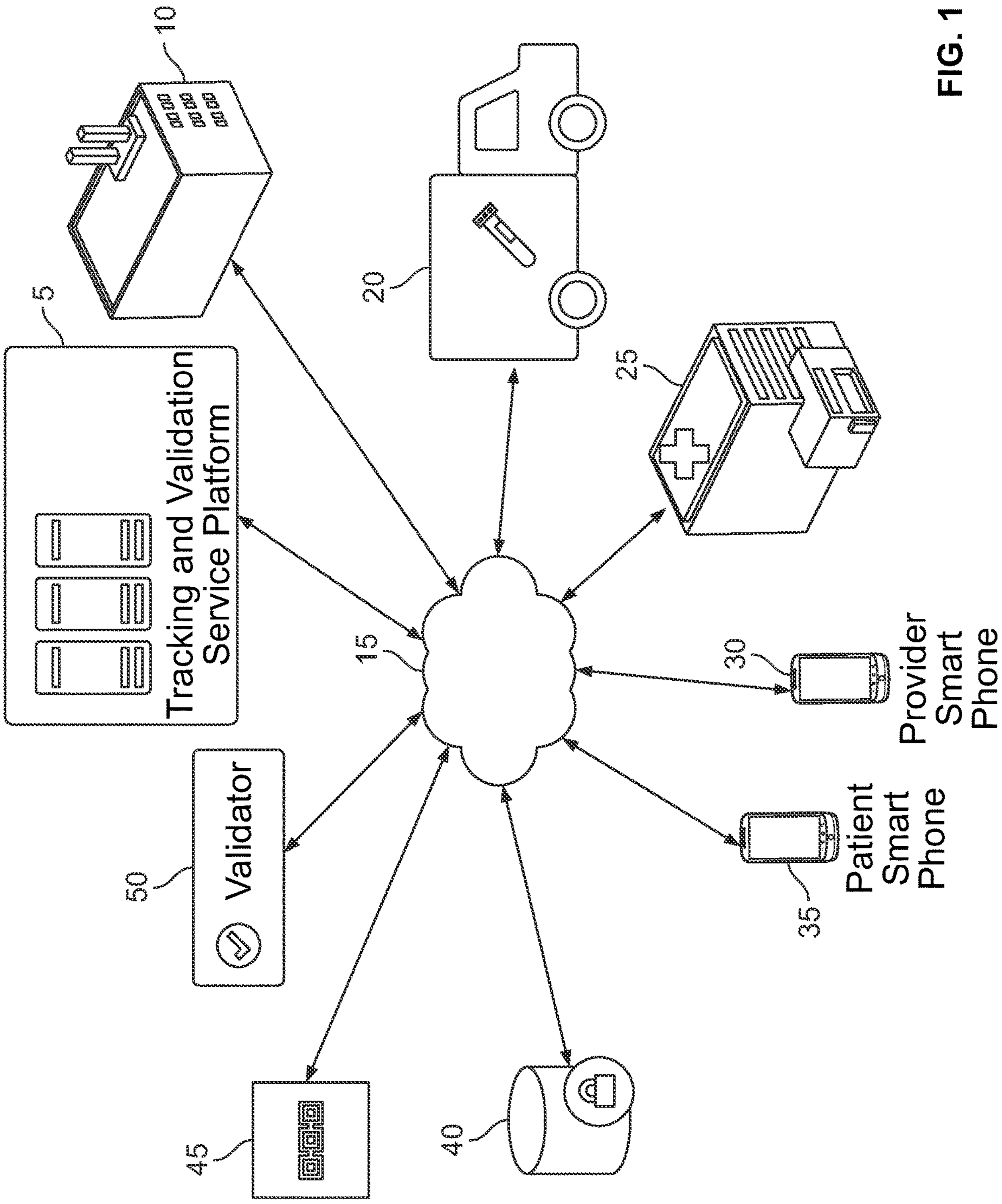
FIG. 1 is an illustration of a network of entities for illustrating tracking of a health-related test kit.

Implementations of the systems, processes, and techniques described in this specification can be used to record, track, authenticate, and validate various different types of health status information. For example, health status information can include a vaccination or immunization status, a test result (e.g., for a communicable disease, presence of antibodies, a medical condition), treatment status, or the like. Health status information can also include the health safety of a location or physical space (e.g., whether the space has implemented cleaning or other safety protocols designed to protect the health of occupants). The processes, systems, and techniques are described and illustrated in the specification using certain examples, such as tracking test kits or validating the immunization status of an individual (e.g., a patient participating in the system, also referred to interchangeably as a test or patient participant), but the processes, systems, and techniques may also be used for other suitable purposes and other health status information.

In some implementations, the techniques can be used for tracking testing (e.g., using test kits) and immunization status. Each person and entity in an overall testing and/or immunization process can register with a health status monitoring service and their identification can be recorded in a service platform. Thereafter, the identity of an individual or an entity can be authenticated against the information stored in the service platform. Similarly, an identifier for each test kit can be registered in the service platform (e.g., by the manufacturer of the test kit). The chain of custody (e.g., from manufacturer to distributor to hospital and intervening trusted delivery services, including the individuals involved in the process), testing individuals (e.g., healthcare agents participating in the system, also referred to as a healthcare agent participant), tested individuals, actions taken with the test kits (e.g., administration of the test, processing of the test to produce test results), delivery of test results, and subsequent verification of test results (e.g., by an individual who verifies health status information, also referred to as a verifying participant) can also be recorded in the service platform. Chain of custody tracking can similarly be applied to vaccine doses, medications, or other objects involved in overall healthcare treatment.

The authenticity and validity of test results or immunity status can be confirmed using the service platform. For example, test results can be retrieved using an app associated with the service platform by authenticating the identification of a patient participant and retrieving test results associated with that patient participant using the service platform. As another example, vaccination status can be retrieved using the app associated with the service platform by authenticating the identification of a patient participant and retrieving records associated with that patient participant using the service platform. The service platform has the ability to authenticate identities and record events to a distributed ledger. The platform can also have the ability to respond to queries to validate events that have occurred in the past and the participants in those events.

The service allows patient participants to have a digital identity that can allow them to track their health information related to a virus or other medical status or condition and to have the ability to share their health status with others. A software application can be used to show a patient participant's current testing status as well as a previous record of exposure to a virus, as evidenced by the outcomes of testing. Participants can also be certified as to their status by respective medical or governmental bodies. These certifications (e.g., immunity certificates or immunization passports) can be shared by the patient with others, such as employers, businesses, and other people at their discretion. In some implementations, a digital wallet can be created on a participant's mobile phone to store their health status or certification status in a secure, auditable platform that can be shared with others.

Test kits or vaccines can be delivered through a secure supply chain platform to allow for a complete chain of trust from the origin to the delivery to the healthcare provider or patient participant. Test kit or vaccine manufacturers, distributors and purchasers can access tracking and ownership information throughout the lifecycle of the kit or vaccine dose. Patient participants can view detailed information about the healthcare provider (or agent participant) and test kits or vaccines administered to them.

Using these techniques, events are recorded in blockchain or other distributed ledger, where a participant token represents each participant (tested or vaccinated individual, healthcare professional, manufacturer, etc.), and a test kit or vaccine dose token represents each test kit or vaccine dose. Event actions between participants and test kits or vaccine doses are recorded. In some implementations, not all activities are recorded—just certain events such as the production of a test kit or vaccine, the administration of a test or vaccine to a patient participant, the test result, and the patient participant's immunity status.

FIG. 1 depicts a network of entities for illustrating tracking of a test kit. Initially, a test kit manufacturer 10 registers with a platform 5 through a network 15. In general, all communications are conducted through the network 15, which may include the Internet, private networks, and/or other communication networks, alone or in combination. The platform 5 can be implemented as a server system that includes one or more servers, which may be centralized or distributed. The registration can be performed by the test kit manufacturer 10 itself or by an authorized agent of the entity that maintains the platform 5 using a process for authenticating the identity of the manufacturer. The manufacturer (and other entities discussed below) can be authenticated using trusted third-party validators 50 (e.g., using a trusted identity provider, such as Auth0). Any or all of the entities that participate in the process may be authenticated in this manner. Also, as part of the registration, test kits (e.g., a type or model number of test kit) are assigned to the manufacturer (or a division thereof) and roles are assigned to company participants (e.g., employees authorized to perform various tasks).

The test kit manufacturer 10, as test kits are produced and shipped, sends test kit manifests and/or a data stream to an inbound API to the platform 5. The test kit data is loaded by serial number into the platform 5 and validated (e.g., by validating that the serial number is unique and/or complies with a serial number convention used by the manufacturer and the test kit data is identified in the platform 5 as a valid test kit. Test kits can be tracked by an assigned object identifier for the manufacturer (e.g., as assigned by the platform) or a key identifier (e.g., a quantum key) and a serial number (e.g., for the individual product). The key identifier can include at least a digital key or utility token, which is maintained or stored in a distributed ledger 45 or blockchain (e.g., Ethereum), uniquely associated with the manufacturer. Although depicted as an entity for convenience of illustration, persons of ordinary skill will understand the distributed ledger 45 is decentralized across a large geographic area and a large number of storage devices managed by diverse entities. In some cases, the key identifier may further be associated with a physical key (e.g., unique quantum dots embedded in each test kit). The test kits can, in turn, be identified by an individual assigned object product token/identifier or a quantum key. In some cases, a batch of test kits may have a single, shared serial number. The test kits in the batch may be assigned a shared assigned object product token or quantum key, or each test kit may be assigned an individual assigned object product token or quantum key.

In some situations, a healthcare provider 25 that manages the testing process sets up a service provider in the platform and links to a number of health-kits (e.g., that are produced by the manufacturer 10 and shipped or allocated to the healthcare provider 25). The service provider may perform the actual testing on behalf of the healthcare provider. The linked health-kits are the health-kits shipped to, or provided to, that service provider. The healthcare provider can also assign other company participants (e.g., healthcare provider employees/roles or service provider employees/roles) or can enable an "auto-join with company credentials" functionality and can specify credentials (e.g., CompanyID, authenticator, etc.) for an agent of the healthcare provider in the platform. Logistics providers or distributors 20 for the manufacturer, and test sites for the healthcare provider 25 are also set up in the platform 5. These entities (e.g., identity, location, etc.) can be defined by the test kit manufacturer or healthcare provider or by an authorized agent of one them or by an agent of the entity that maintains the platform. In general, all actions taken by an entity are performed by an agent (e.g., an employee, contractor, employee of a contractor entity, etc.) of that entity.

Thereafter, test kits can be tracked using the platform 5 to the test site (which may be at a healthcare provider 25 facility or at a different location). For example, the transfer of the test kits from the manufacturer to a distributor and from the distributor to the service provider can be recorded by the platform 5 and assigned a token that is recorded in the distributed ledger 45. The transfer can be recorded based on a physical transfer (e.g., through an electronic communication with the platform when possession of the test kits passes from one entity to the next) or based on a virtual transfer (e.g., through an electronic communication with the platform when a batch of test kits is allocated or shipped to a particular service provider or healthcare provider).

When a test or patient participant arrives at the test site, the test participant can download an app (i.e., a software application) that is securely managed by the platform 5 to the test participant's mobile device 35 (e.g., a smart phone) and can perform a validation process using the app (if the test participant has not previously downloaded the app or performed validation). For example, the validation process can include the test participant inputting personal information, the platform 5 confirming that the information is unique and/or that the test participant is authorized to register through the app, and validating the test participant credentials (e.g., by sending an email or text message to the test participant that requires the test participant to confirm the account). Alternatively, the healthcare provider 25 or its agent can use their version of the app on a provider smart phone 30 to register and validate the test participant using a validation process of the app. The validation process can include scanning (i.e., using the app) one or more required documents (e.g., a driver's license, passport, etc.) and performing facial recognition to establish a participant validated ID, which is sent to the platform and a key identifier is generated and assigned to the test participant. For example, a scanned image from the identification document or documents can be compared to an image captured by a camera on the mobile device on which the app is installed. Facial recognition software built into the mobile device or accessed over an Internet connection can be used to confirm a match. The identification confirmation can be recorded by the platform and a corresponding token can be recorded to the distributed ledger 45. In a typical implementation, any number of provider smart phones 30 and patient smart phones 35 are in use simultaneously. In some implementations, there may be no difference between provider smart phones 30 and patient smart phones 35 other than, in some cases, the app version that exists on each smart phone. Moreover, any smart phone may be able to operate as a provider smart phone 30 or a patient smart phone 35 at any given time.

Using a provider version of the app, the healthcare provider agent selects a test kit and scans the bar code (or alternatively enters the serial number) and assigns it to the test participant (e.g., by selecting an "Assign" option to assign the test kit to the test participant). As a result, an identifier of the test kit and an identifier of the test participant are sent to the platform 5, which records the association and records a corresponding token in the distributed ledger 45. If the test participant has self-registered through the app, the test participant can simply show a participant card, which can be displayed on the participant's mobile device screen in the app, to the healthcare provider agent, who scans the test participant's bar code (or other encoded identifier) displayed on the participant card into the platform, and the participant's identity is associated with the test (i.e., a link between the test participant and the particular test is recorded by the platform). If the health care provider agent entered the test participant information, the agent links it to the test participant (e.g., by selecting a "Link" option to associate the kit with the test participant record). Each of these actions can be recorded in the distributed ledger 45 and/or identifying data sent to the platform 5.

When a test result is returned to the healthcare provider agent, the test receptacle is scanned using the app and appropriate choices for the result are selected in the app, and the agent confirms the selections (e.g., by clicking a "Test Result Verified" option via the app on a provider smart phone 30). If the test participant is using the app, the test participant can immediately review the test results in the app. If the test participant was entered by the healthcare provider agent and the test participant specified an email address or other contact information, the test participant can be notified (e.g., via email) that the test results are available and then can go to a platform portal and sign up to view his or her participant card and test results.

All test participant data including test results can be stored in secure (e.g., HIPAA compliant) data storage 40, through which only authorized healthcare providers have access to the patient test data.

In some implementations, the platform 5 stores the data regarding the test kit and the test participant, while corresponding tokens for confirming the authenticity and validity of the data can be stored in the distributed ledger 45. In other implementations, the platform 5 does not maintain all of the data regarding a test kit and a test participant. Rather, the platform may only store tokens (which may actually be stored in the distributed ledger 45) that can be used to validate that certain events occurred, that a participant's identity was verified, and the outcome of a particular test (e.g., for purposes of displaying an immunity certificate). The data maintained in the distributed ledger 45 can be used to verify and audit that a test kit is authentic, that the test was administered to a particular participant, that a particular result was obtained, and that the test participant has a particular immunity status (e.g., by validating that the test outcomes for a patient match required criteria for different status levels of clearance, which may be coded, for example, as red, yellow, and green). Other data may be stored in external, third party databases.

Rulesets (referred to as modes of transport) may be defined in the platform 5 and/or the distributed ledger 45 that can be used to define a relationship between a participant company and a product so that events can be recorded in the distributed ledger 45. Manufacturers may only have access to modes of transport until the test kit is delivered to the healthcare provider or its agent. Healthcare providers may have access to the modes of transport until the test kit is used. Test participants can have access to their information through the platform portal and app.

Other participants in the service can include governments (e.g., governing bodies of a particular civic area such as a nation, state, province or county), non-governmental organizations (e.g., an organization that is independent of any government, such as the United Nations or World Health Organization), researchers, and certifying authorities (e.g., an entity that authorizes the use of test kits to define specific outcomes or that certifies the identity of participants or entities). Each of these participants can be granted suitable levels of access to data in the platform 5.

In some implementations, the system can include a web interface in addition to or instead of the test participant and healthcare provider apps.

The primary tracking identifiers can include the assigned object product, a key identifier or quantum key for the test kit, a serial number/bar code for the test kit, a participant verified ID, and an immunity (or health) certificate for the test participant. Tracking can be used by anyone or by authorized parties to determine the current location of test kits or vaccine does. Test kit outcomes can be authenticated by a third party (e.g., a laboratory that processes the administered test kit) to determine an immunity status of a participant).

Figure 2:
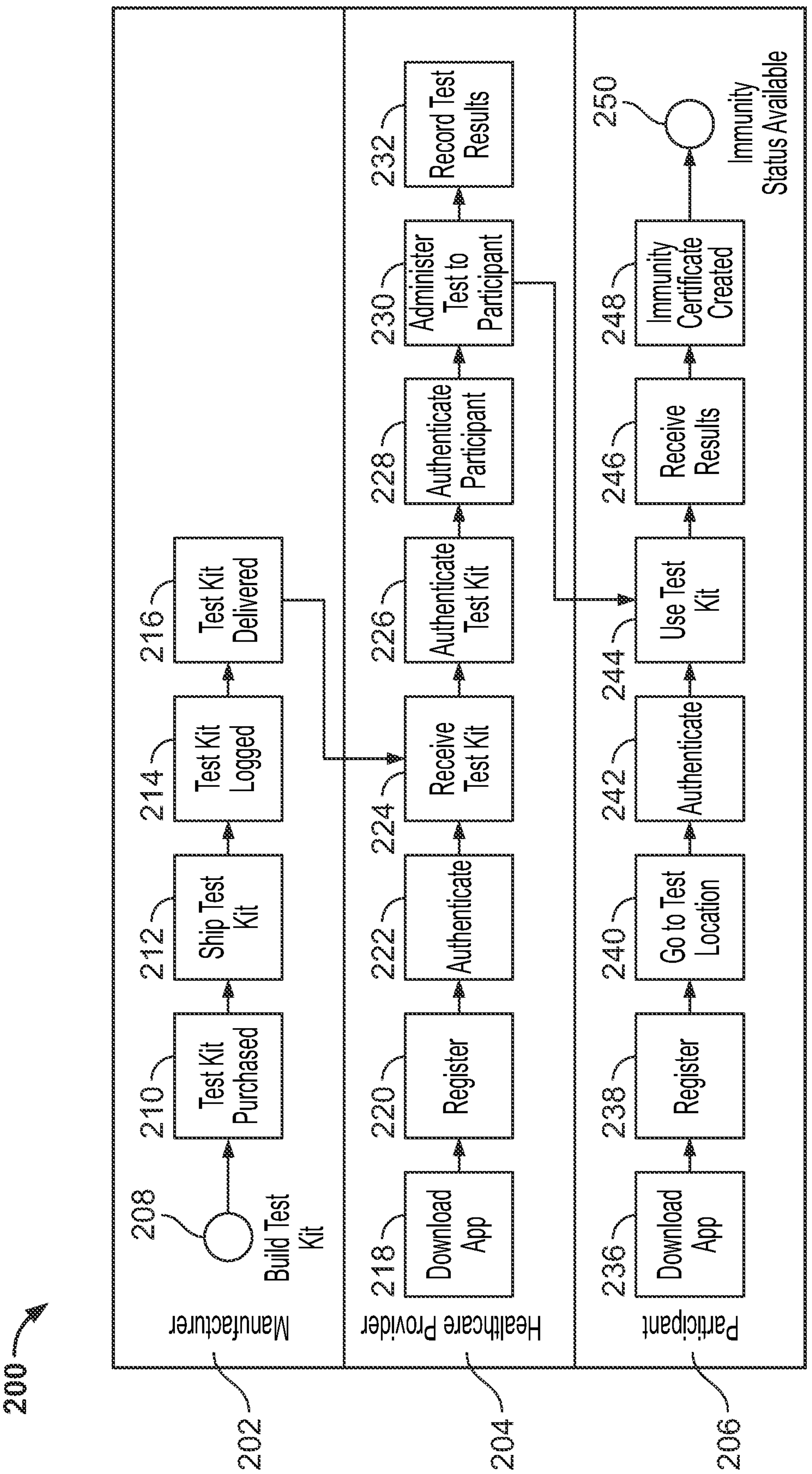
FIG. 2 is a flow diagram illustrating a process for generating a verifiable health status certificate.

FIG. 2 is a flow diagram illustrating a process 200 for generating a verifiable health status certificate. The process 200 involves actions performed by a manufacturer 202, a healthcare provider 204, and a participant 206. The manufacturer 202 builds a test kit at 208 and the test kit is purchased by a healthcare provider 204 at 210. The manufacturer 202 ships the test kit to the healthcare provider at 212 and logs the test kit with a health status tracking server system or platform at 214 by sending identification information (e.g., a serial number or bar code identifier) for the test kit (or a batch of test kits) and an identification of the healthcare provider to the tracking platform, which records the identification information and assigns a corresponding digital token. The identification information may also include an identification of the delivery service used for delivery. Updates as to the delivery status and/or location of the test kit can also be provided by the delivery service throughout transit and recorded by the tracking platform. The test kit is delivered at 216.

Prior to receiving the test kit, an agent of the healthcare provider 204 downloads the app at 218 and registers with the tracking platform at 220 (e.g., by providing identification information and credentials for acting on behalf of the healthcare provider 204). Similarly, the patient participant 206 downloads the app at 236 and registers with the tracking platform at 238.

When the agent of the healthcare provider 204 is ready to receive the test kit, the agent authenticates with the app (or with the tracking platform through the app) at 222. The test kit is received by the agent of the healthcare provider 204 at 224 and authenticates the test kit at 226. For example, the agent can use the app to scan the bar code on the test kit, which the app transmits to the tracking platform. The tracking platform can validate that the test kit is authentic by comparing the received bar code information and the identity of the healthcare provider 204 against the previously recorded information received from the manufacturer 202. If there is a match, the tracking platform can return a verification to the healthcare provider agent's app.

When the patient participant 206 is ready to be tested, the patient participant 206 travels to the test location at 240 and authenticates via the app at 242. The agent of the health care provider 204 verifies the identity the patient participant 206 at 228 by, for example, checking a physical identification card (e.g., a driver's license). In some cases, the agent can capture an image of the identification card, which can be stored and/or tokenized on the tracking platform. The agent participant administers the test to the patient participant 206 at 230 and the patient participant 206 uses the test kit at 244. The patient participant 206 can, for example, scan the test kit barcode using the app, or the agent participant can associate the test kit with the patient participant 206 by scanning the test kit barcode and a displayed code on the patient participant's app and sending the paired information to the tracking platform. When the test results are received, the health care provider 204 records the test results via the app at 232, and the test results are recorded to the tracking platform. As a result, the test results are sent to the patient participant 206, and the patient participant 206 receives the results at 246. The tracking platform also creates an immunity certificate documenting the test results at 248. The immunity status certificate is then available for use by the patient participant (e.g., to present to third parties) at 250.

In some implementations, the patient participant can validate that a particular test kit is an authentic test kit and that a provider is legitimate by using the app to scan a bar code or entering serial number information for the test kit and scanning credentials associated with the healthcare provider agent participant. These credentials can be confirmed against data previously recorded in the platform.

Figure 3:
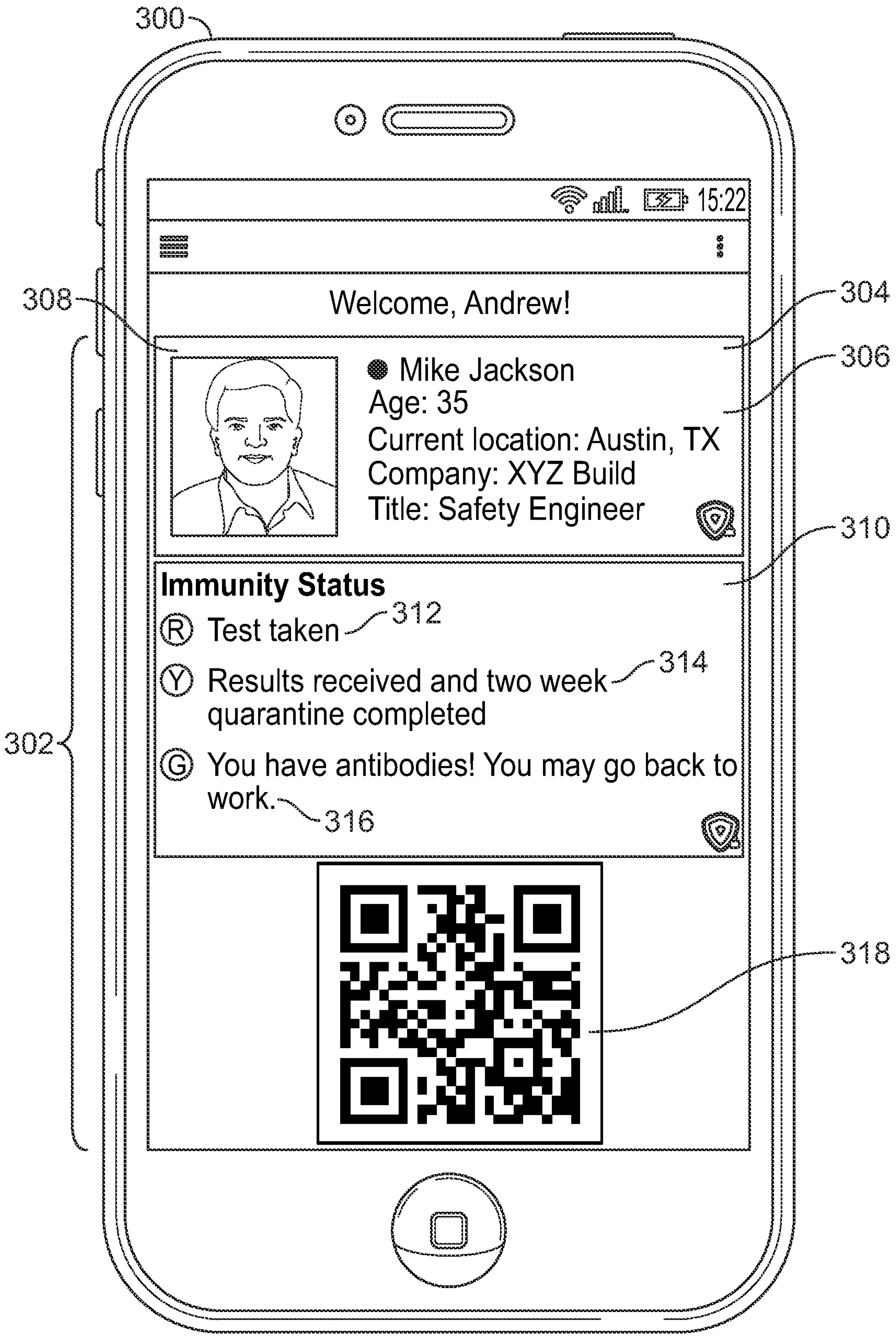
FIG. 3 is an illustration of a mobile device displaying an immunity certificate, as generated through the process of FIG. 2.

FIG. 3 is an illustration of a mobile device 300 displaying a health status (e.g., an immunity) certificate 302, as generated through the process of FIG. 2, on the app. In this example, the health status certificate 302 is illustrated as an immunity certificate, although in other implementations, the health status certificate 302 may provide other health status information (e.g., vaccination status or status of a health test outcome). The immunity certificate 302 includes the name 304 of the patient participant along with other identifying information 306 and a photo 308 of the patient participant. In addition, the immunity status 310 is displayed. For illustrative purposes, different possible immunity statuses are depicted. Initially, the immunity status may reflect at 312 that a test has been taken but results have not yet been received. In such a case, the immunity status may be coded "red" to reflect that the patient participant does not yet have immunity. Later, the immunity status may reflect at 314 that test results have been received and a two-week quarantine period has been completed. Still later, the immunity status may reflect at 316 that the participant is cleared for normal activity. The immunity certificate 302 also includes a QR code 318 that can be scanned using an app on a third-party device to verify the immunity status through the tracking platform.

Figure 4:
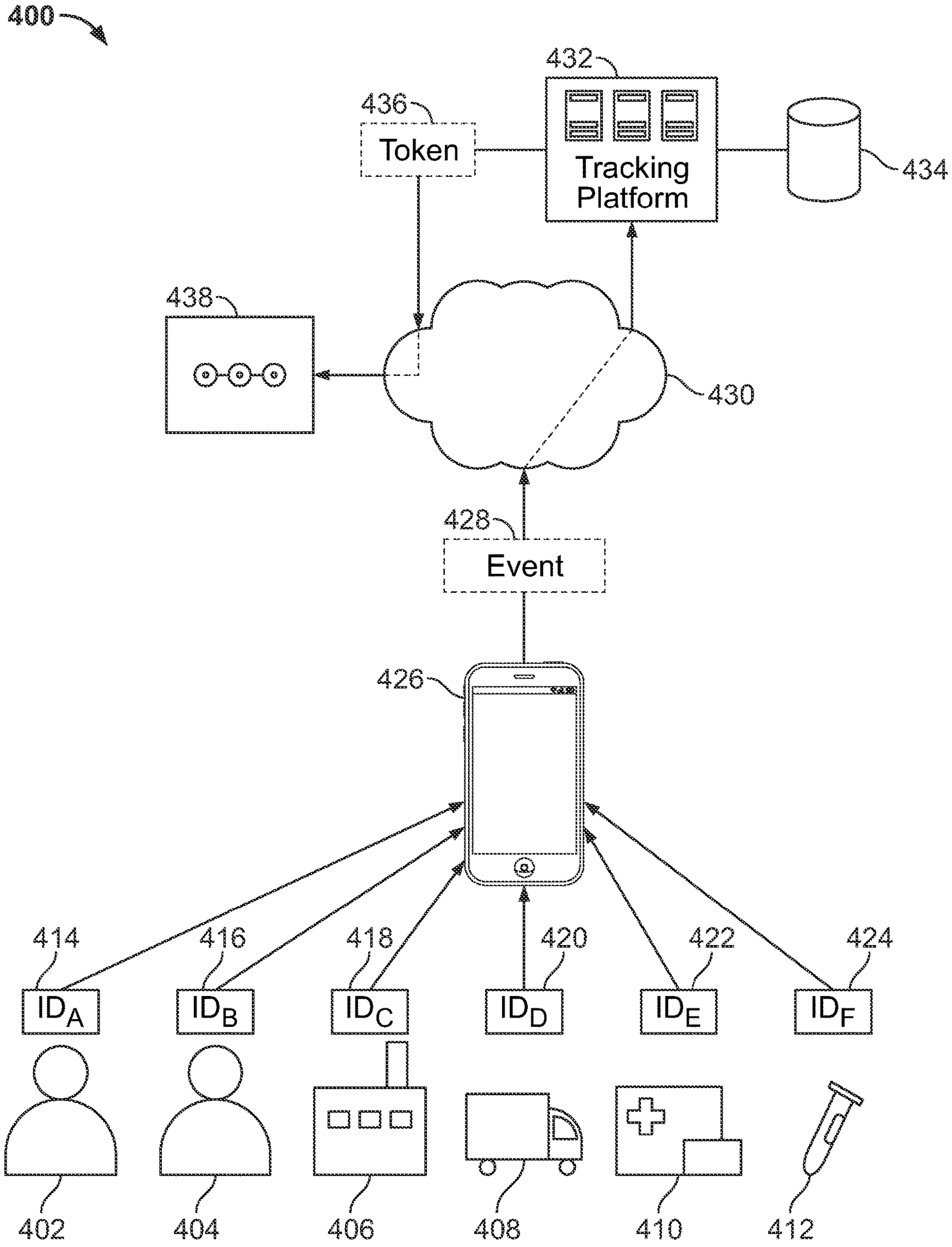
FIG. 4 is a diagram of a process for recording events and identities in the tracking platform.

FIG. 4 depicts a process 400 for recording events and identities in the tracking platform. In in various implementations, different levels of detail can be recorded in the tracking platform. For example, some implementations can involve tracking a chain of custody of a test kit, a vaccine dose, or other health-related objects from manufacture through final use or disposal. Other implementations can simply record an association between a test kit or vaccine dose and the receiving patient participant. The process of recording events is similar for each event. The primary distinctions relate to the number of participants, entities, or objects involved in the events. FIG. 4 depicts a number of possible participants, entities, or objects for a given event. For example, events can involve entities, such as a manufacturer, a shipping company, or a health care provider. Events can also involve individual participants, such as a patient, an employee or other agent of a health care provider, or an employee of a manufacturer or shipping company. Events can be performed using test kits, vaccine doses, medications, or other objects. Entities, participants, and objects can have associated identifiers that can be recorded in association with an identification of or data regarding the event itself.

A first example event can involve two entities, two participants, and an object, each with its own identifier. For example, a manufacturer (a first entity 406) may ship a test kit (an object 412) using a shipping company (a second entity 408). An employee (a first participant 402) of the manufacturer may physically transfer the test kit to an employee (a second participant 404) of the shipping company. When the event occurs, the respective identifiers 414, 416, 418, 420, and 424 can be collected using an app on a mobile device 426. The app can collect the respective identifiers by, for example, scanning bar codes, a QR code displayed on the app of a registered user, identifying the authenticated user of the app, and identifying entities with which the participants are associated. The identity of each registered entity, participant, or object can also be authenticated with the tracking platform using credentials or other identifying information. The registered user can select an option to cause the app to send the identifiers along with an identification 428 of the event itself to the tracking platform 432 as a secure communication via the Internet 430. The event and the associated identifiers can be recorded by the tracking platform 432 in a database 434. The tracking platform can also initiate generation of a token 436 corresponding to the recorded data for storage in the distributed ledger 438.

A second example event can involve one entity, two participants, and an object, each again with its own identifier. For example, an agent (a first participant 402) of a healthcare provider (a third entity 410) may administer a test kit (an object 412) to a patient (a second participant 404). When the event occurs, the respective identifiers 414, 416, 422, and 424 can be collected using an app on a mobile device 426. The app can collect the respective identifiers by, for example, scanning a bar code on the test kit, a QR code displayed on the app of the patient, and identifying the authenticated agent user of the app and the healthcare provider with which the agent is associated. The registered agent user can select an option to cause the app to send the identifiers along with an identification 428 of the event itself to the tracking platform 432. The event and the associated identifiers can be recorded by the tracking platform 432 in a database 434, and the tracking platform can initiate generation of a token 436 corresponding to the recorded data for storage in the distributed ledger 438.

Various other events can be recorded in a similar manner to, for example, track and record the chain of custody of a test kit, vaccine dose, or other health-related objects. In addition, test results can be recorded as an event, along with an identifier of a healthcare provider that analyzed the test, an identifier of an agent who verified and recorded the test result, and an identifier of the patient who was previously associated with the test kit. Other events may occur as a result of certain criteria being met. For example, health status information can be updated (e.g., as a result of passage of a quarantine period), which can be updated in the database 434 of the tracking platform 432, resulting in a new token 436 being generated and stored in the distributed ledger 438. The various events can subsequently be validated using data stored in the database 434 of the tracking platform 432 and the corresponding token 436 stored in the distributed ledger.

Figure 5:
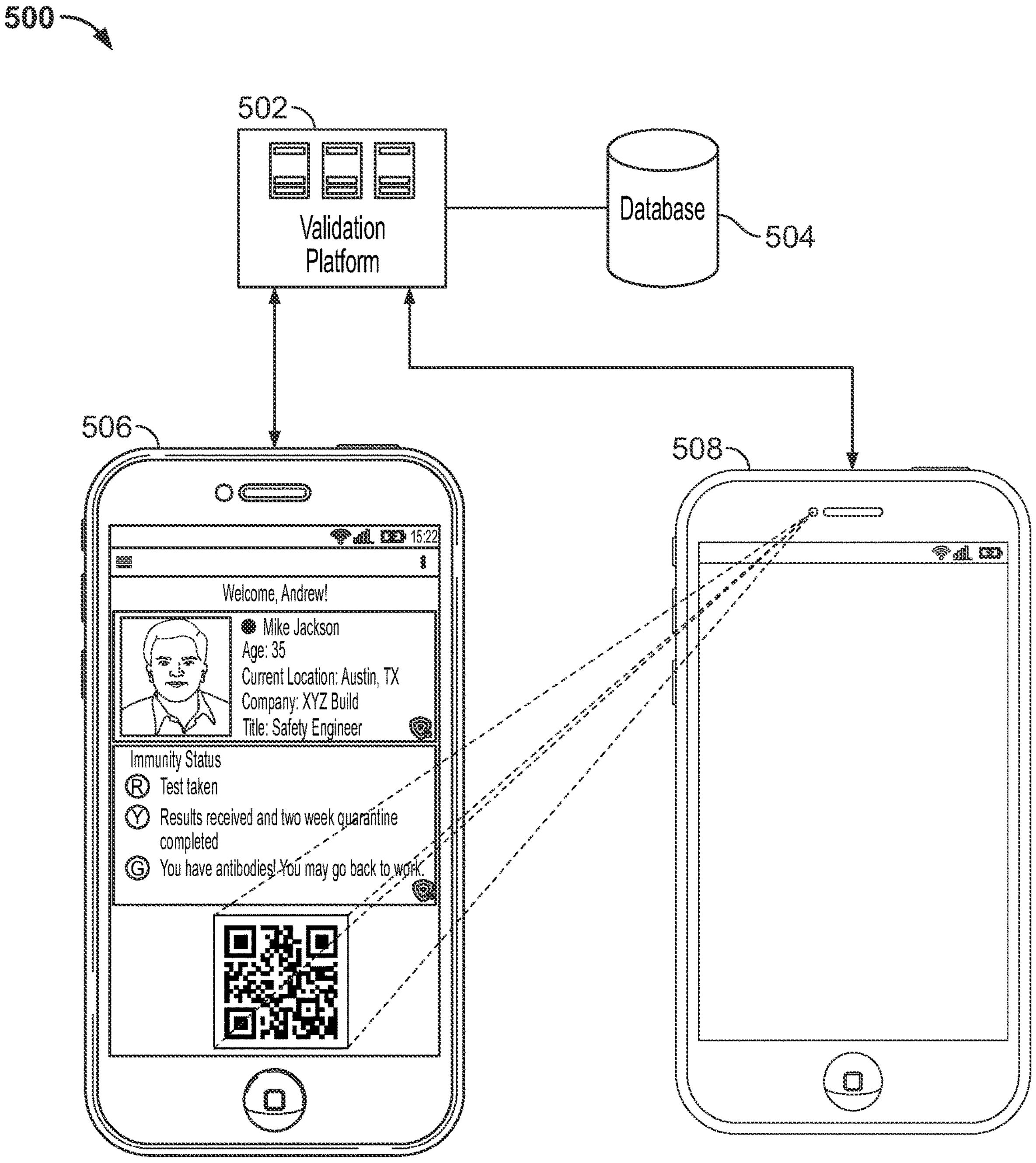
FIG. 5 is an illustration of a validation system for validating health status information.

FIG. 5 is an illustration of a validation system 500 for validating health status information. The validation system 500 can be used to validate health status information generated using the tracking platform described above. The validation system 500 includes a validation platform or server system 502. In some implementations, the validation platform 502 and the tracking platform described above can be the same platform or associated components of the same platform. Alternatively, the validation platform 502 can be a separate server system. Typically, however, the validation platform 502 has access to the data stored as part of the tracking process and to the tokens stored in the distributed ledger.

The validation system 500 further includes a database 504 storing user identification and health data and a plurality of user devices 506 and 508. Although only two user devices 506 and 508 are depicted for illustrative purposes, the validation system 500 typically includes any number of user devices. The user devices 506 and 508 can be mobile devices, such as a smartphone or a tablet. A first user device 506 includes an installed software application (i.e., an app) programmed to allow a user to authenticate to the validation platform 502, to retrieve health status information, and to display the health status information. The second user device 508 includes an installed software application (i.e., an app) programmed to allow a user to authenticate and validate health status information detected from the first user device 506. In some implementations, the software application installed on each user device 506 in 508 can be different applications, while in other implementations, the application can include functionality to selectively display health status information and to authenticate and validate health status information. In addition, the application can also include the functionality described above for recording events associated with a testing, vaccination, or other health-related process.

When a user of the first user device 506 desires to share health status information (e.g., for purposes of demonstrating a vaccination or immunization status), the user navigates to a screen that displays a health status certificate, such as the health status certificate described in connection with FIG. 3. The health status certificate provides the desired health status information. A user of the second user device 508 can navigate to a screen that allows the second user device 508 to capture an image of the QR code displayed on the first user device 506. As depicted in FIG. 5, the QR code is captured using the front camera, but the image can similarly and conveniently be captured using the back camera. The software application on the second user device 508 processes the captured image to extract the QR code and serialize the data therein for transmission to the validation platform 502. The software application on the second user device 508 transmits the serialized data to the validation platform 502 as part of a request for verification of the health status information.

The validation platform 502 uses the received data to identify a digital token associated with the QR code. Using the digital token, the validation platform 502 retrieves corresponding health status information and identification information for the associated participant from the database 504. The validation platform 502 then transmits the retrieved health status information and participant identification information to the second user device 508. The participant identification information can include the name, image, and other identifying information associated with QR code as stored in the database 504. The software application on the second user device 508 displays the identification information and the health status information received from the validation platform 502 so that the user of the second user device 508 can verify a match with the identity of the user of the first user device 506 and the health status information displayed on the first user device 506.

Figure 6:
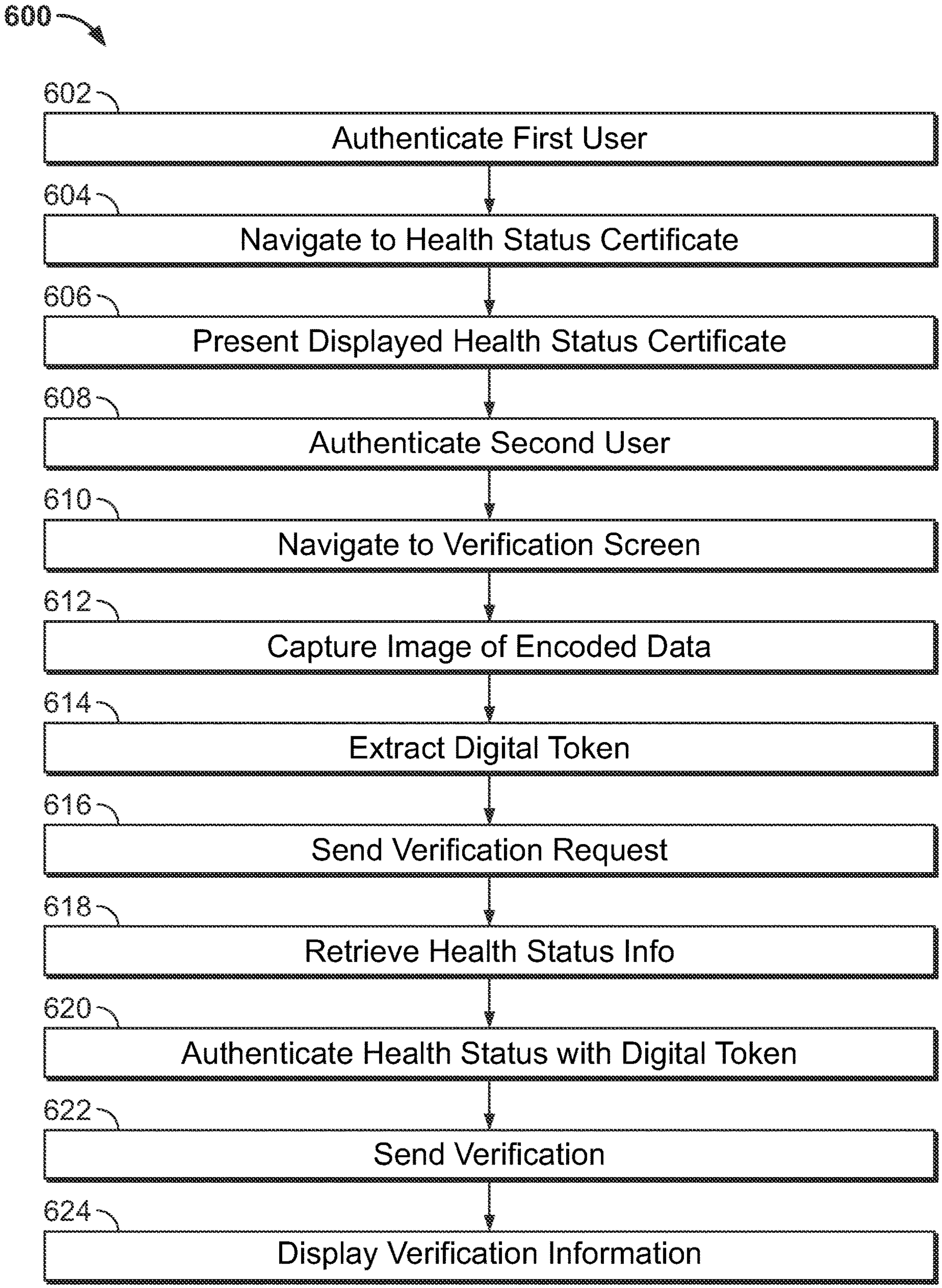
FIG. 6 is a flow diagram of a process for allowing an individual or entity to perform validation of health status information of another person or entity.

FIG. 6 is a flow diagram of a process 600 for performing validation of health status information. The process can be performed by the validation system 500 described above in connection with FIG. 5. Initially, a first user desiring to present health status information, such as an immunization passport or immunity certificate, to another person opens a software application on a first mobile device and authenticates with a validation system through the software application at 602. The first user navigates to a screen that displays a desired health status certificate at 604. The health status certificate includes a human-readable visual display of health status information and encoded data (e.g., a QR code, bar code, or other image for encoding an identifier) referencing a digital token previously stored in a distributed ledger. The digital token is associated with at least one health-related event for the first user. For example, the digital token may be associated with the user having satisfied a set of criteria used to determine whether the user is considered to be fully vaccinated or has immunity to a particular virus.

The first user then presents the display screen to a second user of a second user device (e.g., a smartphone) at 606. After authenticating with the validation system through a software application on the second user device at 608, the second user navigates at 610 to a screen on the software application that allows the user to perform a verification of the health status certificate displayed on the first user device. The second user positions the second user device to capture an image of the encoded data displayed on the first user device at 612. The software application on the second user device processes the detected image to extract the reference to the digital token encoded in the image at 614. The software application on the second user device transmits a request to verify the health status certificate including a serialized version of the extracted reference to the verification platform at 616.

After receiving the request, the verification platform uses the received data (i.e., the serialized version of the extracted reference and/or the digital token) to retrieve corresponding health status information from a database at 618 and to authenticate the retrieved health status information based on the digital token at 620. The verification platform then transmits a communication to the second user device to verify the health status certificate at 622. The software application on the second user device displays the verification information (e.g., identification information and health status information as stored by the verification platform) at 624. The second user can then confirm that the health status certificate displayed on the first user device and the user identity matches the verification information received from the verification platform. In some cases, if the verification platform is unable to authenticate the health status information or if the verification information does not match, the second user can conclude that the health status information is invalid or fraudulent.

The verification can be used to ensure that the health status information complies with a predetermined set of criteria for determining the health status information. For example, the verification performed by the validation platform can ensure a verified chain of possession of a health test kit or a vaccination dose, a predetermined period of time since a positive test result for a communicable disease, a verified source of a health test kit or a vaccine, a recordation of a sequence of events in a distributed ledger, administration of a vaccination or a health test by an authorized entity, or verifying certification of a health status by a governmental, healthcare provider, or other certifying entity. Similarly, the health status information (e.g., as displayed and stored) can include an indication that the first user has received a vaccination or a positive antibody test, that a predetermined period of time since a positive test result for a communicable disease, a certification from an authorizing authority, or compliance with a required quarantine.

In some implementations, other techniques for detecting encoded data on a user device to perform verification can be used. For example, encoded data on a participant's mobile device can be communicated to a device for verification using near field communications and/or credentials stored in a digital wallet on the user device.

In some implementations, the software application and the verification platform can allow a user to have multiple health status profiles, each having potentially different health status information. For example, different health status profiles can correspond to immunity or vaccination for different diseases or to different sets of criteria as may be required by different entities to demonstrate vaccination or immunization status. One health status profile may be associated with requirements of an employer to go to work, while another health status profile may be required to be able to travel on an airline. The user can also decide which certifying authorities are displayed for each profile. A certifying authority can be any governmental, private, or other entity that is sets forth standards for assessing or categorizing health status, that authenticates or validates test results, immunization status, or other health status, or that serves as a trusted source for verification of health status. The user can select the appropriate health status profile as part of selectively displaying health status information to another person.

In some cases, the techniques described in this specification can alternatively be used to enable owners of offices, restaurants, entertainment venues and other venues (i.e., "spaces") to allow occupants a way to validate the current health status of a site. By using the tracking platform and the verification platform to monitor and measure the safety efforts of a space owner and to allow that to be displayed regularly on or in connection with a space (e.g., at an entrance to the site or space) with a QR code validated health safety certificate for the space (i.e., much like an individual health status certificate), occupants can feel secure that the best efforts have been made to help them stay healthy. In such an implementation, the health safety certificate for the space may be displayed on a printed paper or sign instead of displayed on a mobile device.

By recording and tracking the use of procedures for cleaning, disinfecting, and the like for spaces, safety status indicator (e.g., red, yellow, and green designations to indicate varying levels of compliance) can be displayed on or at the space. The software application can verify the status, space owners can monitor the overall health of their spaces, and individuals can check the status of any space they will be occupying.

A space owner (e.g., analogous to a healthcare provider) can assigns a procedure (e.g., analogous to a test kit or health kit) to a space (e.g., analogous to a participant) and records the outcome (e.g., analogous to a test kit result). Procedure agents (e.g., analogous to healthcare provider agents) perform the procedures (e.g., cleaning, testing, UV treatments, etc.) and update outcomes of the procedures on a regular basis. The safety status indicator can be updated based on each outcome (e.g., as with a participant's health status).

Based upon a rule set (pass/fail for each procedure, like a test kit) that can define rules from differing certifying authorities, the safety status indicator can be generated with a safety status and a QR code. A card can then be printed out with a normal printer and placed in a visible spot (a door or wall) that can be easily scanned by an individual with the software application.

Thus, in addition to being able to define rules for validating health status on individuals, a certifying authority can specify rules for a location (i.e., a space) to let people know the health status of a location or physical space. For example, a movie theater may reserve different individual theaters for participants who have different health status levels, or a hotel chain may certify certain rooms "green" or "yellow" to let participants know what kinds of services they can expect when checking in for a room certified as "green" or "yellow."

In some implementations, the software application may include a geolocation option, and geo-fencing status alerts for people as they move between spaces. Rental cars, hotel rooms, and workspaces (e.g., by scanning QR codes associated with each through the software application) can enable users (e.g., through the software application) which certifying authorities have performed what testing and what level of maintenance is needed for a space to be considered safe. Similar statuses and procedures can be used for validating compliance with other procedures (e.g., safety, cleaning, testing, etc.) by other entities, including healthcare providers, agents, manufacturers, and the like.

In general, the system, processes, and techniques can provide one or more of the following advantages, alone or in any combination. The system can authenticate each participant, test kit manufacturers, and healthcare providers to verify that the participant has been tested and to verify the result. Results of a test can be provided to medical professionals, caregivers, and patients in an on-demand fashion so that the patient is in control of who gets the information. The system authenticates the test kit, the provider of the test kit, and the supply chain from provider to patient creating a verifiable and immutable chain of trust. Events, interactions, and data collection can be logged on a distributed ledger-based data store so every activity can be traced to a point in time and data is known to be authentic. The system provides data dependent on local requirements to appropriate healthcare organizations and governments. The system can help ensure that an individual's identity and testing status is authenticated and validated (e.g. that an individual's identity was corroborated using physical identification such as a passport, a driver's license or other official documentation), that the individual was tested on a particular date using a certified test kit, and that the test result has been properly recorded. The system can ensure that the identity of the person administering the test (such as a medical professional, a caregiver, or an individual self-administering the test) is authenticated and approved (e.g. that a physician's or nurse's identity and their license credentials were corroborated by physical identification, certifications, or licenses as required by a particular jurisdiction or agency). The system can help ensure that the test kit used is authentic and has been shipped from a validated manufacturer to the point of use via a verifiable chain of custody or trust (e.g. the test kit is not a counterfeit, is from an approved manufacturer, and has been transported to the place of use in a secure manner). The software application presents an individual's verifiable health and immunization status as a user-friendly and intuitive immunization passport or health status certificate, which can be configured to comply with immunization, testing and health status processes and definitions operating in different states, regions, and countries.

Implementations of the subject matter and the functional operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions tangibly stored on a computer readable storage device for execution by, or to control the operation of, data processing apparatus. In addition, the one or more computer program products can be tangibly encoded in a propagated signal, which is an artificially generated signal, e.g., a machine-generated electrical, optical, or electromagnetic signal, that is generated to encode information for transmission to suitable receiver apparatus for execution by a computer. The computer readable storage device can be a machine-readable storage device, a machine-readable storage substrate, a memory device, or a combination of one or more of them.

A computer program (also known as a program, software, software application, script, or code) can be written in any form of programming language, including compiled or interpreted languages, declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, mobile device, a personal digital assistant (PDA), a mobile audio or video player, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CDROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations of the subject matter described in this specification can be implemented in a computing system that includes a backend component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such backend, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other.

While this specification contains many implementation details, these should not be construed as limitations on the scope of the invention or of what may be claimed, but rather as descriptions of features specific to particular implementations of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method comprising:

displaying health status information on a display of a mobile device;

detecting encoded data on the mobile device using an image sensor, wherein the encoded data includes a reference to a digital token previously stored in a distributed ledger to record at least one health-related event associated with the displayed health status information;

transmitting a serialized representation of the detected encoded data to a server system, wherein the server system is adapted to retrieve corresponding health status information and authenticate the retrieved health status information based on the digital token;

receiving a communication from the server system providing verification of the health status information, wherein the digital token is a quantum key comprising quantum dots.

2. The method of claim 1 wherein the communication includes a verification of an identity of at least one individual associated with the health status information.

3. The method of claim 1 wherein the verification includes a verification that the health status information complies with a predetermined set of criteria for determining the health status information.

4. The method of claim 3 wherein the predetermined set of criteria defines a verified chain of possession of at least one of a health test kit or a vaccination dose.

5. The method of claim 3 wherein the predetermined set of criteria defines a predetermined period of time since a positive test result for a communicable disease.

6. The method of claim 3 wherein the predetermined set of criteria defines a verified source of at least one of a health test kit or a vaccine.

7. The method of claim 3 wherein the predetermined set of criteria defines a recordation of a sequence of events in a distributed ledger.

8. The method of claim 1 wherein the health status information identifies at least one of:

receipt of a vaccination;

a positive antibody test:

passage of a predetermined period of time since a positive test result for a communicable disease;

a certification from an authorizing authority; or a quarantine status.

9. The method of claim 1 wherein the communication includes a verification that at least one of a vaccination or a health test was administered by an authorized entity.

10. The method of claim 1 wherein the health status information corresponds to a selected health status profile of a plurality of health status profiles for an individual, with each health status profile associated with a different set of criteria for determining the health status information for the corresponding health status profile of the plurality of health status profiles, wherein the selected health status profile corresponding to the health status information is selected by a user of the mobile device.

11. A system comprising:

a database storing records associated with a plurality of registered users;

a server system communicably connected to the database, wherein the server system is adapted to:

receive a request from a first remote device for a verification of health status information displayed on a second remote mobile device, wherein the request is sent by the first remote device in response to detecting encoded data displayed on the second remote mobile device;

the encoded data includes a reference to a digital token previously stored in a distributed ledger to record at least one health-related event associated with the health status information; and the request includes the reference to the digital token;

retrieve health status information corresponding to the digital token;

authenticate the retrieved health status information using the distributed ledger based on the digital token; and transmit a communication to the first remote device providing verification of the health status information, wherein the digital token is a quantum key comprising quantum dots.

12. The system of claim 11 further comprising the first remote device and the second remote mobile device, wherein:

the first remote device comprises a mobile device including the image sensor and includes a software application adapted to receive an image of a display of the second remote mobile device and to decode the encoded data; and the second remote mobile device includes a software application adapted to allow a user of the second remote mobile device to selectively display the health status information.

13. The system of claim 11 wherein the communication includes a verification of an identity of at least one individual associated with the health status information.

14. The system of claim 11 wherein the verification includes a verification that the health status information complies with a predetermined set of criteria for determining the health status information.

15. The system of claim 11 wherein the health status information corresponds to a selected health status profile of a plurality of health status profiles for an individual, with each health status profile associated with a different set of criteria for determining the health status information for the corresponding health status profile of the plurality of health status profiles, wherein the selected health status profile corresponding to the health status information is selected by a user of the mobile device.

16. A computer storage medium encoded with a computer program, the program comprising instructions that when executed by data processing apparatus cause the data processing apparatus to perform operations comprising:

detecting an image displayed on a display of a mobile device using an image sensor, wherein the image is associated with health status information displayed on the display of the mobile device;

decoding data encoded in the detected image to obtain a reference to a digital token previously stored in a distributed ledger to record at least one health-related event associated with the health status information;

sending a request to a server system for verification of the health status information, wherein the request includes a serialized representation of the detected encoded data to a server system and the server system is adapted to authenticate the health status information based on the digital token;

receiving a communication from the server system providing verification of the health status information, wherein the digital token is a quantum key comprising quantum dots.

17. The computer storage medium of claim 16 wherein the communication includes a verification of an identity of at least one individual associated with the health status information, and the program further comprises instructions to display the verification on a user interface.

18. The computer storage medium of claim 16 wherein the verification includes a verification that the health status information complies with a predetermined set of criteria for determining the health status information, and the program further comprises instructions to display the verification on a user interface.

* * * * *